United States Patent
He et al.

(10) Patent No.: US 10,467,898 B2
(45) Date of Patent: Nov. 5, 2019

(54) DRIVING BEHAVIOR CORRECTION METHOD AND DEVICE BASED ON INTERNET OF VEHICLES

(71) Applicants: ZHEJIANG GEELY AUTOMOBILE RESEARCH INSTITUTE CO., LTD, Taizhou (CN); ZHEJIANG GEELY HOLDING GROUP CO., LTD, Hangzhou (CN)

(72) Inventors: Jinpeng He, Taizhou (CN); Dayong Zhou, Taizhou (CN); Weiguo Liu, Taizhou (CN); Chengming Wu, Taizhou (CN); Qingfeng Feng, Taizhou (CN)

(73) Assignees: ZHEJIANG GEELY AUTOMOBILE RESEARCH INSTITUTE CO., LTD, Taizhou (CN); ZHEJIANG GEELY HOLDING GROUP CO., LTD, Hangzhou (CN)

( * ) Notice: Subject to any disclaimer, the term of this patent is extended or adjusted under 35 U.S.C. 154(b) by 0 days.

(21) Appl. No.: 15/750,439

(22) PCT Filed: May 20, 2016

(86) PCT No.: PCT/CN2016/082762
§ 371 (c)(1),
(2) Date: Feb. 5, 2018

(87) PCT Pub. No.: WO2016/197806
PCT Pub. Date: Dec. 15, 2016

(65) Prior Publication Data
US 2018/0308353 A1    Oct. 25, 2018

(30) Foreign Application Priority Data
Jun. 10, 2015 (CN) .......................... 2015 1 0317341

(51) Int. Cl.
*G08G 1/0962* (2006.01)
*B60W 50/14* (2012.01)
(Continued)

(52) U.S. Cl.
CPC .......... *G08G 1/09626* (2013.01); *A61B 5/08* (2013.01); *A61B 5/18* (2013.01); *B60K 28/066* (2013.01);
(Continued)

(58) Field of Classification Search
None
See application file for complete search history.

(56) References Cited

U.S. PATENT DOCUMENTS

2011/0313740 A1    12/2011  Ikeda et al.
2013/0110310 A1*   5/2013  Young ................. B60W 40/09
                                                       701/1
(Continued)

FOREIGN PATENT DOCUMENTS

CN    102265319 A    11/2011
CN    103093612 A    5/2013
(Continued)

OTHER PUBLICATIONS

International Search Report and Written Opinion of the International Searching Authority for International Patent Application No. PCT/CN2016/082762 dated Jul. 26, 2016, with English translation, 17 pages.

*Primary Examiner* — Leon Viet Q Nguyen
(74) *Attorney, Agent, or Firm* — Alston & Bird LLP (57) ABSTRACT

The disclosure relates to an Internet of Vehicles technology, and particularly to a driving behavior correction method and device based on the Internet of Vehicles. The driving behavior correction method based on the Internet of Vehicles comprises: a first information acquirer acquiring informa-
(Continued)

tion about a vehicle in real time, and a second information acquirer acquiring vehicle condition information about the other surrounding vehicles on a travelling road in real time; and a determination unit arranged in the vehicle or at a cloud determining in real time, according to the information about the vehicle and the vehicle condition information about the surrounding vehicles, whether a driving behavior of the vehicle is dangerous, and if so, issuing a driving behavior correction prompt to the driver of the vehicle, which can intervene in and correct the driving behavior of the driver in real time.

10 Claims, 5 Drawing Sheets

(51) Int. Cl.
| | | |
|---|---|---|
| *B60K 28/06* | (2006.01) | |
| *B60W 40/09* | (2012.01) | |
| *G08G 1/0967* | (2006.01) | |
| *G06K 9/00* | (2006.01) | |
| *A61B 5/08* | (2006.01) | |
| *A61B 5/18* | (2006.01) | |
| *B60Q 9/00* | (2006.01) | |
| *B60W 50/00* | (2006.01) | |
| *H04L 29/08* | (2006.01) | |

(52) U.S. Cl.
CPC ............... *B60Q 9/00* (2013.01); *B60W 40/09* (2013.01); *B60W 50/0098* (2013.01); *B60W 50/14* (2013.01); *G06K 9/00845* (2013.01); *G08G 1/096775* (2013.01); *B60W 2050/0077* (2013.01); *B60W 2550/20* (2013.01); *H04L 67/10* (2013.01); *H04L 67/12* (2013.01)

(56) References Cited

U.S. PATENT DOCUMENTS

| | | | | |
|---|---|---|---|---|
| 2015/0360697 | A1* | 12/2015 | Baek | ...................... B60W 40/09 701/23 |
| 2017/0120906 | A1* | 5/2017 | Penilla | ................. G05D 1/0011 |

FOREIGN PATENT DOCUMENTS

| | | |
|---|---|---|
| CN | 103198685 A | 7/2013 |
| CN | 103310202 A | 9/2013 |
| CN | 103350663 A | 10/2013 |
| CN | 103514758 A | 1/2014 |
| CN | 104392622 A | 3/2015 |
| CN | 104952249 A | 9/2015 |
| EP | 2381431 A1 | 10/2011 |
| JP | 2007-000280 A | 1/2007 |
| JP | 2007-226666 A | 9/2007 |

* cited by examiner

DRIVING BEHAVIOR CORRECTION METHOD AND DEVICE BASED ON INTERNET OF VEHICLES

CROSS-REFERENCE TO RELATED APPLICATIONS

This application is a national phase entry of International Application No. PCT/CN2016/082762, filed May 20, 2016, which claims priority to Chinese Patent Application No. 201510317341.6, filed on Jun. 10, 2015, the entire contents of which are incorporated herein by reference.

TECHNICAL FIELD

The present invention relates to an Internet of Vehicles technology, and particularly to a driving behavior correction method and device based on the Internet of Vehicles.

BACKGROUND ART

Figure 5:
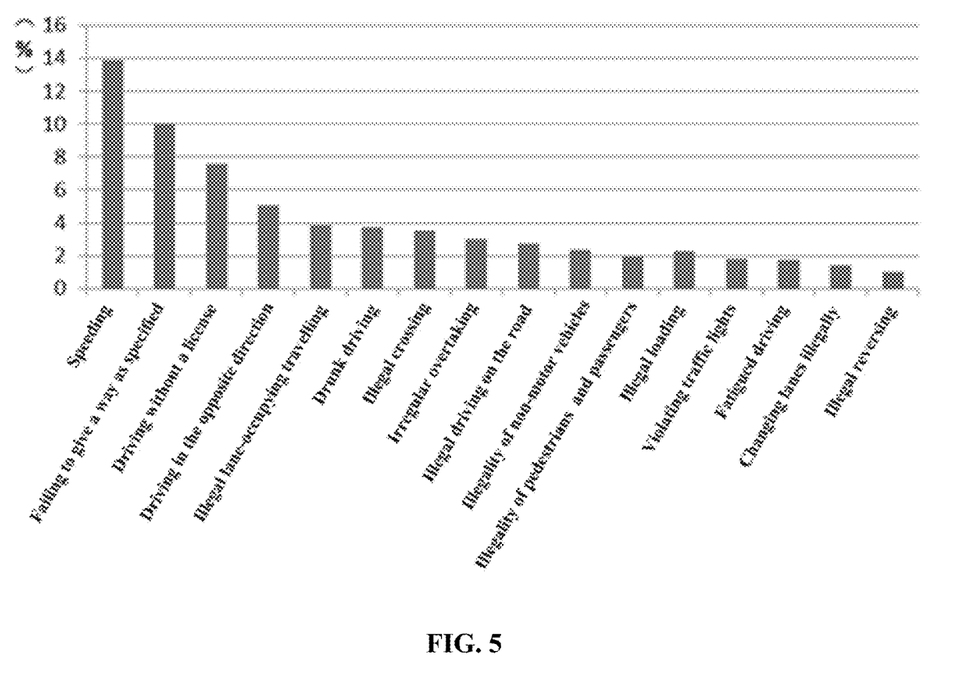
FIG. 5 is a statistical chart of traffic accidents.

As shown in the statistical chart of traffic accidents of "Annual Statistical Report on Road Traffic Accidents of the People's Republic of China" in FIG. 5, the illegal driving behavior of automobile drivers is the main cause of traffic accidents in our country. Detecting/determining and correcting the illegal driving behavior of a driver in daily travelling can effectively prevent the traffic accidents and avoid the losses brought to people and properties due to the traffic accidents.

In the prior art, the illegal driving behavior of a driver is generally monitored by a static camera at a fixed position, and since the monitored road section is limited and the monitoring means is single, the driving behavior of the driver cannot be monitored in real time and there is also the possibility of omitting the detection of the illegal driving behavior. In addition, even if all of the illegal driving behaviors can be detected, the disastrous consequence caused by the illegal driving behavior cannot be compensated.

SUMMARY OF THE INVENTION

An object of the present invention is to provide a technology that can prompt, in real time, a driver to correct an illegal driving behavior, in order to avoid the consequences of the illegal driving behavior.

A further object of the present invention is to enable all illegal driving behaviors of a driver to be monitored in real time and as comprehensively as possible.

According to one aspect of the present invention, the present invention provides a driving behavior correction method based on the Internet of Vehicles, the method comprising:

a first information acquirer acquiring information about a vehicle in real time, wherein the information about the vehicle comprises: vehicle condition information about the vehicle, driver state information, and travelling road information about a road on which the vehicle travels, and a second information acquirer acquiring vehicle condition information about the other surrounding vehicles on the travelling road in real time;

a determination unit arranged in the vehicle or at a cloud determining in real time, according to the information about the vehicle and the vehicle condition information about the other surrounding vehicles, whether a driving behavior of the vehicle is dangerous, and if so, issuing a driving behavior correction prompt to the driver of the vehicle, and if not, not issuing the correction prompt.

Further, the method also comprises: the determination unit determining in real time, according to the information about the vehicle and the vehicle condition information about the other surrounding vehicles, whether the driving behavior of the vehicle is illegal, and if so, uploading the illegal driving behavior to the cloud.

Further, in the method, the correction prompt information is downloaded from the cloud or read from a memory in the vehicle.

Further, in the method, the first information acquirer and the second information acquirer are the same vehicle-mounted sensor.

Further, in the method, the first information acquirer and the second information acquirer are different vehicle-mounted sensors, wherein the first information acquirer detects and obtains, in real time, the vehicle condition information about the vehicle, the driver state information about the vehicle, and the travelling road information about the road on which the vehicle travels; and wherein the second information acquirer acquires the vehicle condition information about the surrounding vehicles from the cloud in real time.

According to another aspect of the present invention, the present invention provides a driving behavior correction system based on the Internet of Vehicles, the system comprising:

a first information acquirer for acquiring information about a vehicle in real time, wherein the information about the vehicle comprises: vehicle condition information about the vehicle, driver state information, and travelling road information about a road on which the vehicle travels;

a second information acquirer for acquiring vehicle condition information about the other surrounding vehicles on the travelling road in real time;

a determination unit arranged in the vehicle or at a cloud for determining in real time, according to the information about the vehicle and the vehicle condition information about the other surrounding vehicles, whether a driving behavior of the vehicle is dangerous; and a prompt unit for issuing a driving behavior correction prompt to the driver of the vehicle if the driving behavior of the vehicle is dangerous, and not issuing the correction prompt if not.

Further, the system also comprises a transmission unit, wherein the transmission unit is configured to, if the determination unit determines in real time that the driving behavior of the vehicle is an illegal driving behavior according to the information about the vehicle and the vehicle condition information about the other surrounding vehicles, upload the illegal driving behavior to the cloud.

Further, in the system, the transmission unit is further configured to download the correction prompt information from the cloud or read the correction prompt information from a memory in the vehicle, and to provide the correction prompt information to the prompt unit.

Further, in the system, the first information acquirer and the second information acquirer are the same vehicle-mounted sensor.

Further, in the system, the first information acquirer and the second information acquirer are different vehicle-mounted sensors, wherein the first information acquirer detects and obtains the information about the vehicle in real time; and wherein the second information acquirer acquires the vehicle condition information about the surrounding vehicles from the cloud in real time.

According to the method or system described above, the vehicle condition information comprises at least one of:
vehicle position information;
vehicle speed information;
acceleration information; and
steering information.

According to the method or system described above, the driver state information comprises at least one of:
respiratory information;
eye opening and closing information; and
attention information.

The present invention determines, based on information about a vehicle and vehicle condition information about surrounding vehicles, whether a driving behavior of the vehicle is dangerous, and it should be particularly noted that the dangerous driving behavior herein is not necessarily an illegal driving behavior. As such, even though the driving behavior of the vehicle is not illegal, when it is determined according to various pieces of information that continuing the driving behavior will cause a danger to the vehicle, a driving behavior correction prompt is issued to the driver of the vehicle, which can intervene in and correct the driving behavior of the driver in real time. When the determination unit is arranged at the cloud, the determination unit can update the information about the vehicle and the other vehicles that have been connected to a network in real time, so as to provide a more accurate correction prompt to all the drivers that can connect a network.

According to the detailed description of the particular embodiments of the present invention below in conjunction with the accompanying drawings, the above-mentioned and other objects, advantages and features of the present invention will be more clear to a person skilled in the art.

BRIEF DESCRIPTION OF THE DRAWINGS

Some of the particular embodiments of the present invention will be described below in detail in an exemplary but not limiting way with reference to the accompanying drawings. In the accompanying drawings.

DETAILED DESCRIPTION OF THE EMBODIMENTS

Figure 1:
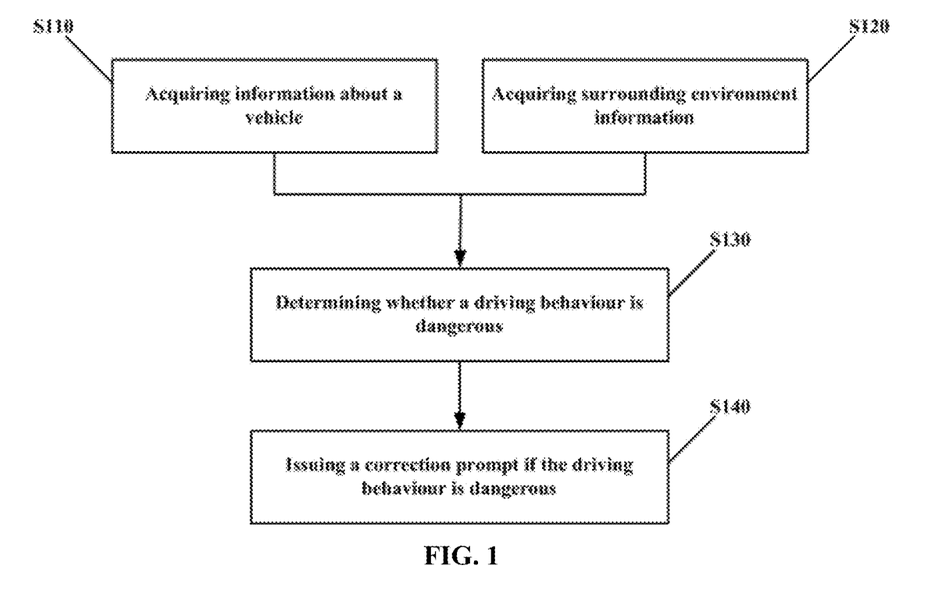
FIG. 1 is a method flowchart of a driving behavior correction method based on the Internet of Vehicles according to one embodiment of the present invention.

As shown in FIG. 1, in the method flowchart of a driving behavior correction method based on the Internet of Vehicles in the present invention, the method can basically comprise:

Step S110, acquiring information about a vehicle. In this step, a first information acquirer acquires, in real time, vehicle condition information about the vehicle, driver state information about the vehicle, and travelling road information about a road on which the vehicle travels.

Step S120, acquiring surrounding environment information. In this step, a second information acquirer acquires vehicle condition information about surrounding vehicles on the travelling road in real time.

Step S130, determining whether a driving behavior is dangerous. In this step, a determination unit arranged in the vehicle or at a cloud determines in real time, according to various pieces of information, whether the driving behavior of the vehicle is dangerous. For example, when the driving behavior of the vehicle falls within the existing definition criteria for danger, it is determined that the driving behavior is dangerous. For example, the definition of danger is: suddenly turning in the process of travelling.

Step S140, issuing a correction prompt if the driving behavior is dangerous. In this step, a driving behavior correction prompt is issued to the driver of the vehicle if the driving behavior is dangerous, and the correction prompt is not issued if not.

It can be seen that the driving behavior correction method based on the Internet of Vehicles according to the present invention determines whether a driving behavior of a vehicle is dangerous based on vehicle condition information about the vehicle, driver state information, travelling road information and vehicle condition information about surrounding vehicles on the travelling road, behavior and it should be particularly noted that the dangerous driving behavior herein is not necessarily an illegal driving behavior. As such, even though the driving behavior of the vehicle is not illegal, when it is determined according to various pieces of information that continuing the driving behavior will cause a danger to the vehicle, a driving behavior correction prompt is issued to the driver of the vehicle. In this way, by means of the driving behavior correction technology based on the Internet of Vehicles in the present invention, the driving behavior of the driver can be intervened and corrected in real time. When the determination unit is arranged at the cloud, the determination unit can update the information about the vehicle and the other vehicles that have been connected to a network in real time, so as to provide a more accurate correction prompt to all the drivers that can connect a network.

As mentioned above, the dangerous driving behavior is not necessarily an illegal driving behavior. In a preferred embodiment of the present invention, the determination unit determines in real time, according to various pieces of information, whether the driving behavior of the vehicle is illegal, and if so, a correction prompt in the form of a voice, an image or a video is issued to the driver and the illegal driving behavior is uploaded to the cloud. The illegal driving behavior will be uploaded to the cloud in real time or at a set time point, and thus such illegal driving behavior will be for example sent to a vehicle management centre for recording, which eliminates the fluke mind of the driver escaping the illegal driving behavior detection and can monitor all the illegal driving behaviors of the driver as comprehensively as possible.

In an embodiment of the present invention, the correction prompt information is downloaded from the cloud. In another embodiment of the present invention, the correction prompt information is read from a memory in the vehicle.

In an embodiment of the present invention, the first information acquirer and the second information acquirer are the same vehicle-mounted sensor. In another embodiment of the present invention, the first information acquirer and the second information acquirer are different vehicle-mounted sensors. The first information acquirer detects and obtains, in real time, vehicle condition information about the vehicle, driver state information about the vehicle, and travelling road information about a road on which the vehicle travels; and the second information acquirer acquires in real time, from the cloud, vehicle condition information about surrounding vehicles on the travelling road.

Figure 2:
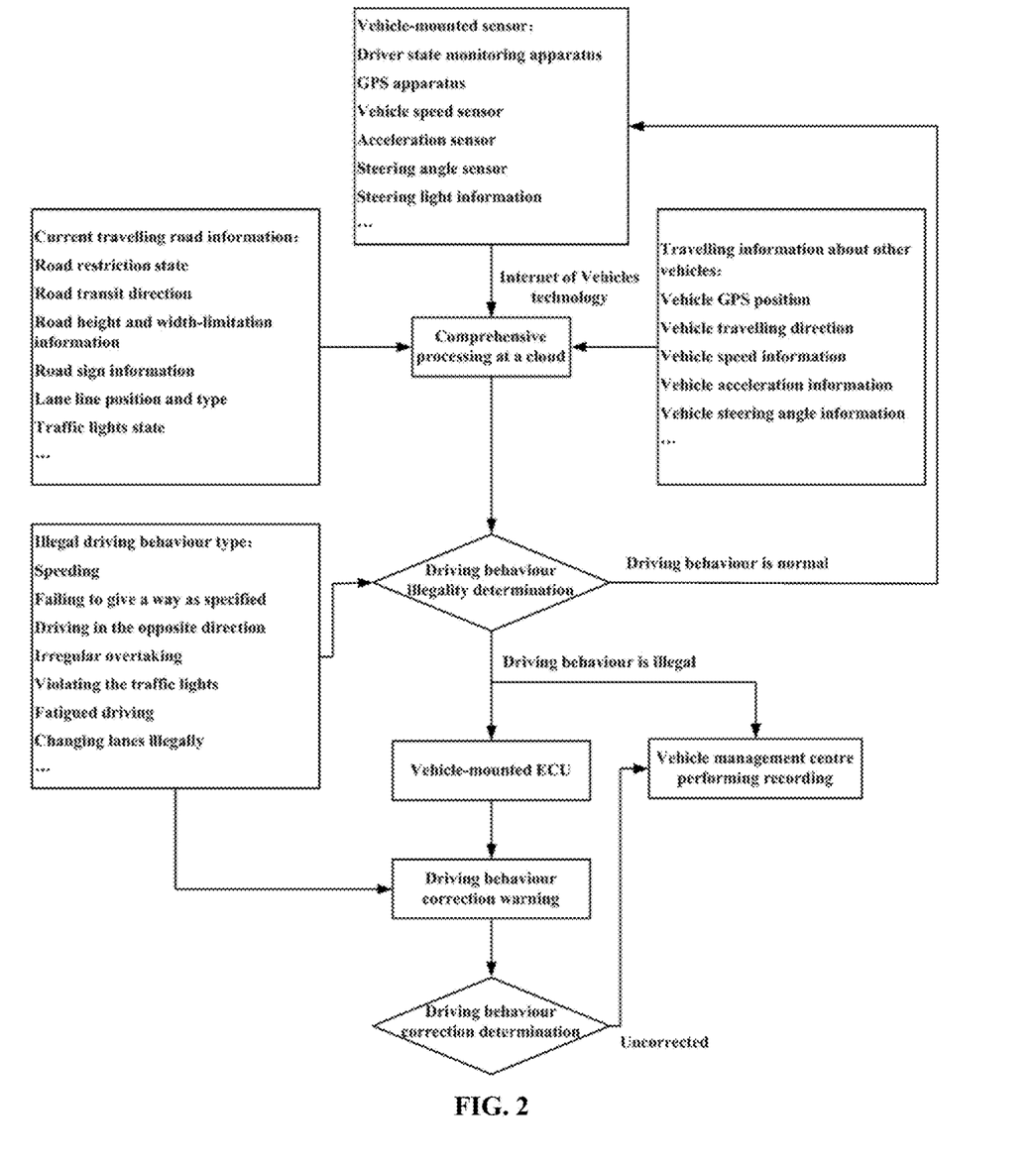
FIG. 2 is a method flowchart according to another embodiment of the present invention.

FIG. 2 is a method flowchart according to another embodiment of the present invention. In FIG. 2, a driver state monitoring apparatus in a vehicle-mounted sensor serving as the first information acquirer detects and acquires driver state information, for example, detecting whether the driver is in a drowsy state or is to enter a drowsy state by means of respiratory information and eye opening and closing information about the driver; detecting whether the driver's attention is focused and whether the driver is in a distracted state by detecting the driver's brain wave information. Vehicle position information in the vehicle condition information about the vehicle is detected by means of a GPS apparatus in the vehicle-mounted sensor. A vehicle speed sensor, an acceleration sensor and a steering angle sensor in the vehicle-mounted sensor determine vehicle speed information, acceleration information and steering information in the vehicle condition information about the vehicle respectively, and the steering information is determined with the aid of steering light information. Moreover, the vehicle-mounted sensor also acquires the current travelling road information (hereinafter, the travelling road is referred to as road for short), a restriction state of the road, a transit direction of the road, height and width-limitation information about the road, signs information about the road, lane line position and type information, and information about traffic lights on the road. For example, after the restriction state of the road is sent to the cloud, it can be ensured that other following networked vehicles will no longer enter the road, thereby saving the transit time of the following vehicles. Similarly, after the height and width-limitation information about the road is provided to the following vehicles, the vehicles with excessive height and width can be prevented from entering the road. The type of illegal driving behavior is pre-stored in the determination unit arranged in the vehicle, that is to say, a well-defined illegal driving behavior is stored in the determination unit in advance. With reference to FIG. 2, various pieces of information mentioned above and driving information about other networking vehicles (vehicle GPS position information, travelling direction information, vehicle speed information, acceleration information and steering information) are all sent to the cloud by means of the Internet of Vehicles technology, and are comprehensively processed by the cloud and then sent to the determination unit for driving behavior illegality determination, in order to determine whether the driving behavior of the vehicle is illegal. As shown in FIG. 2, pre-set illegal driving behaviors include speeding, failing to give a way as specified, travelling in the opposite direction, irregular overtaking, violating traffic lights, fatigued driving, and changing lanes illegally, which are sent to the determination unit. According to the types of pre-set illegal driving behavior and the information transmitted by the cloud, if it is determined that the driving behavior of the vehicle is not illegal, that is, the driving behavior is normal, it is returned to continuously use the vehicle-mounted sensor to detect the vehicle condition information about the vehicle. If it is determined that the driving behavior of the vehicle is illegal, the illegal driving behavior is uploaded to a vehicle management centre of the cloud for recording. At the same time, a vehicle-mounted ECU of the vehicle issues a driving behavior correction warning according to the illegal driving behavior to urge one to make a correction, for example, the driving behavior correction warning can be the turning-on of a yellow light arranged in the vehicle when speeding, and the warning for steering against regulation can be the turning-on of a red light arranged therein. Moreover, for the types of illegal driving behavior provided above, a time period may be set, and if a driver does not correct the illegal driving behavior, the illegal driving behavior is transmitted to the vehicle management centre again. For example, if the driver does not correct the illegal driving behavior, the driver will be subjected to point penalty, and if the illegal driving behavior is corrected within the set time period, the driver will be relieved or exempted from penalty.

Figure 3:
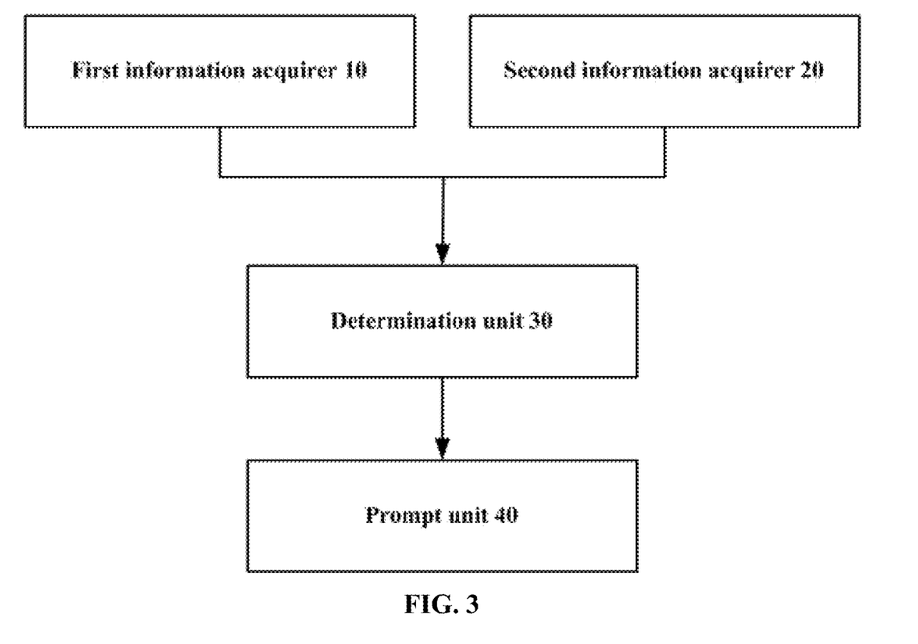
FIG. 3 is a system composition diagram of a driving behavior correction system based on the Internet of Vehicles according to one embodiment of the present invention.

As shown in FIG. 3, the present invention also provides a driving behavior correction system based on the Internet of Vehicles. The system can include a first information acquirer 10, a second information acquirer 20, a determination unit 30 and a prompt unit 40.

The first information acquirer 10 is used for acquiring, in real time, vehicle condition information about a vehicle, driver state information about the vehicle, and travelling road information about a road on which the vehicle travels.

The second information acquirer 20 is used for acquiring vehicle condition information about surrounding vehicles on the travelling road in real time.

The determination unit 30 is arranged in the vehicle or at a cloud for determining in real time, according to various pieces of information, whether a driving behavior of the vehicle is dangerous.

The prompt unit 40 issues a driving behavior correction prompt to the driver of the vehicle if the driving behavior of the vehicle is dangerous, and does not issue the correction prompt if not.

In an embodiment of the present invention, the driving behavior correction system based on the Internet of Vehicles also comprises a transmission unit, wherein the transmission unit is configured to, if the determination unit determines in real time that the driving behavior of the vehicle is an illegal driving behavior according to various pieces of information, upload the illegal driving behavior to the cloud. In another embodiment of the present invention, the transmission unit is further configured to download the correction prompt information from the cloud or read the correction prompt information from a memory in the vehicle, and to provide the correction prompt information to the prompt unit.

In an embodiment of the present invention, the first information acquirer and the second information acquirer are the same vehicle-mounted sensor. In an embodiment of the present invention, the first information acquirer and the second information acquirer are different vehicle-mounted sensors, wherein the first information acquirer detects and obtains, in real time, vehicle condition information about the vehicle, driver state information about the vehicle, and travelling road information about a road on which the vehicle travels; and wherein the second information acquirer acquires in real time, from the cloud, vehicle condition information about surrounding vehicles on the travelling road.

According to the method or system described above, the vehicle condition information comprises at least one of: vehicle position information; vehicle speed information; acceleration information; and steering information.

In the present invention, travelling information about a vehicle (including a vehicle position, a vehicle speed, an acceleration, a steering angle, etc.) and a driver state (including drowsiness, distraction, inattention, etc.) are monitored by a vehicle-mounted sensor in real time; the above-mentioned information is uploaded to a cloud server by means of the Internet of Vehicles technology, is processed and calculated at the cloud in combination with the current travelling road information about the vehicle and surrounding vehicle information to determine whether an illegal driving behavior occurs to the vehicle, and is downloaded to a vehicle driving behavior correction reminding processor via the cloud; and a driving reminding manner is used to correct the illegal driving behavior of the driver, and determine whether the illegal driving behavior is corrected and send the illegal behavior and correction information to the vehicle management centre for recording.

Figure 4:
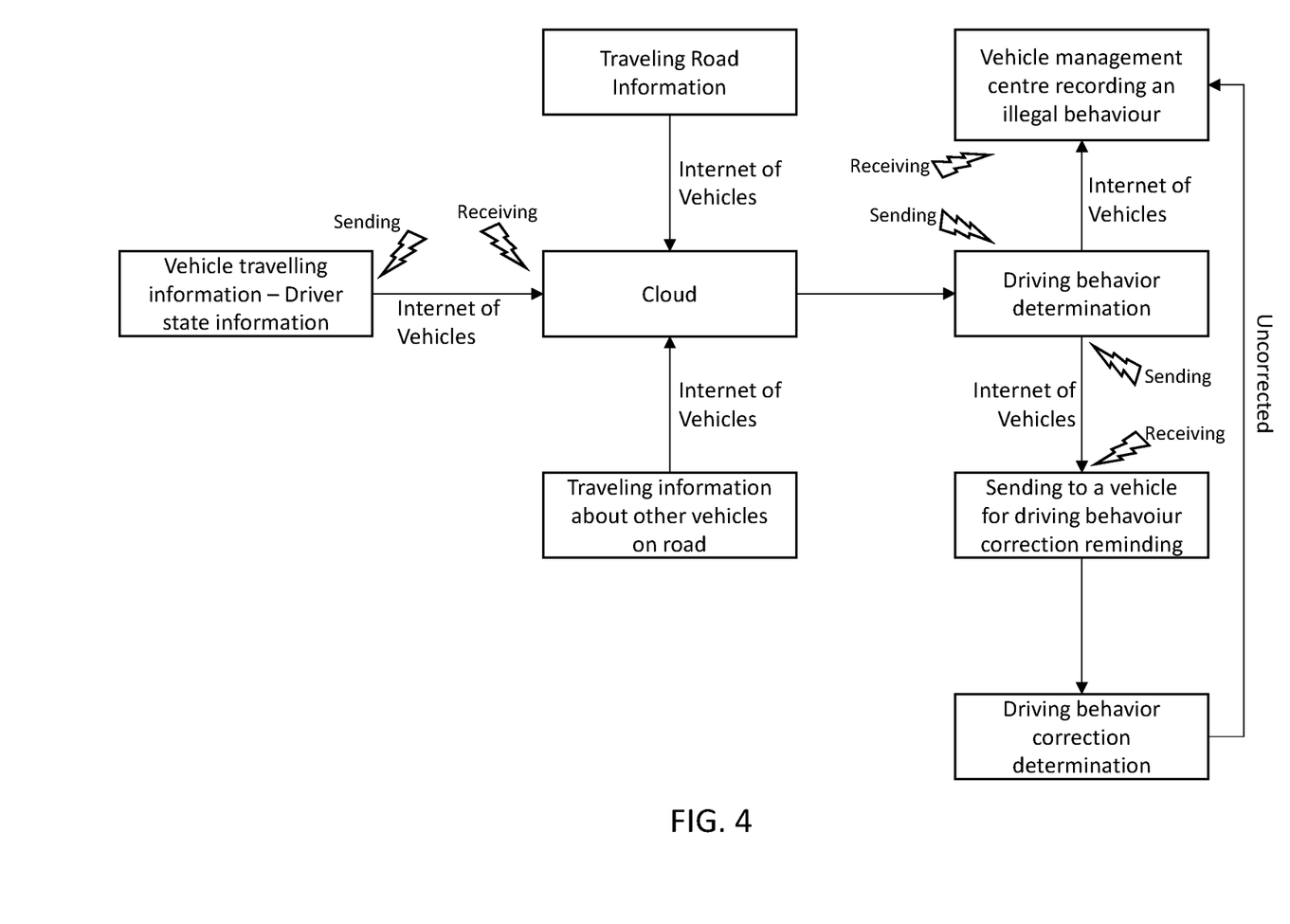
FIG. 4 is a system composition diagram according to another embodiment of the present invention.

As shown in FIG. 4, in this system, vehicle travelling information i.e., vehicle condition information about the vehicle, and driver state information can be monitored by a vehicle-mounted sensor in real time, and data of the above-mentioned information is sent by means of the Internet of Vehicles technology (such as, 3G, 4G or passing the information to a network device like smart phone through WIFI) and received by a server at a cloud. The server at the cloud can also perform comprehensive processing in combination with the current travelling road information about the vehicle sent by the vehicle and driving information about the other networking vehicles on the travelling road, thereby determining whether an illegal driving behavior occurs to the vehicle. If the illegal driving behavior occurs to the vehicle (such as, speeding, driving in the opposite direction, illegal lane-occupying travelling, violating traffic signals, fatigued driving, etc.), the determination information is sent to the vehicle for driving behavior correction reminding, that is, the vehicle receives the determination information to issue a corresponding warning to a driver of the vehicle, and assists the driver of the vehicle to correct the illegal driving behavior, while sending the illegal driving behavior information to the vehicle management centre for recording so as to provide a basis for penalty.

It can be seen that the present invention has the following advantages:

1) the present invention, in combination with the Internet of Vehicles technology, comprehensively processes travelling road information (including a lane line position, a traffic light state, etc.) about a road on which a vehicle travels, vehicle condition information about the vehicle (including a vehicle position, a vehicle speed, an acceleration, a steering angle, etc.) and a driver state (information including drowsiness, distraction, inattention, etc.), such that an illegal driving behavior of a driver can be found in a timely and accurate manner;

2) when monitoring the illegal driving behavior, the present invention can issue a driving behavior correction reminder to the driver and continue to track whether the driver has corrected the illegal driving behavior thereof; and 3) when monitoring the illegal driving behavior, the present invention can send illegal driving behavior information and the corresponding correction information to a vehicle management centre for recording, which can effectively reduce the occurrence of illegal driving behavior.

Various embodiments regarding components in the present invention may be implemented in hardware, or implemented by software modules running on one or more processors, or implemented in combinations thereof. It should be understood for those skilled in the art that a microprocessor or a digital signal processor (DSP) may be used in practice to implement some or all the functions of some or all the components or modules in the device according to the embodiments of the present invention. The present invention can further be implemented as devices or apparatus programs (e.g., computer programs and computer program products) for executing some or all of the methods as described herein. Such programs for implementing the present invention may be stored on a computer-readable medium, or may be in a form of one or more signals. Such signals can be obtained by downloading from an Internet website, or provided on a carrier signal, or provided in any other forms.

Up to this, a person skilled in the art should recognize that although a plurality of exemplary embodiments of the present invention have been shown and described in detail herein, numerous other variations or modifications meeting the principle of the present invention can be directly determined or derived according to the contents disclosed in the present invention. Therefore, the scope of the present invention should be construed and considered as covering all of such other variations or modifications.

The invention claimed is:

1. A driving behavior correction method based on the Internet of Vehicles, comprising:
   a first information acquirer acquiring information about a vehicle in real time, wherein the information about the vehicle comprises:
      vehicle condition information about the vehicle,
      driver state information, and
      travelling road information about a road on which the vehicle travels;
   a second information acquirer acquiring vehicle condition information about the other surrounding vehicles on the travelling road in real time, the driver state information comprising respiratory information, eye opening and closing information and attention information;
   a determination unit arranged in the vehicle or at a cloud determining in real time, according to the information about the vehicle and the vehicle condition information about the surrounding vehicles, whether a driving behavior of the vehicle is dangerous, and if so, issuing a driving behavior correction prompt to the driver of the vehicle, and if not, not issuing the correction prompt; and
   the determination unit determining in real time, according to the information about the vehicle and the vehicle condition information about the surrounding vehicles, whether the driving behavior of the vehicle is illegal, and if so, uploading the illegal driving behavior to the cloud, and sending the illegal driving behavior to a vehicle management centre for recording so as to provide a basis for penalty on the driver, wherein the type of illegal driving behavior is pre-stored in the determination unit.

2. The method according to claim 1, wherein the correction prompt information is downloaded from the cloud or read from a memory in the vehicle.

3. The method according to claim 1, wherein the first information acquirer and the second information acquirer are the same vehicle-mounted sensor.

4. The method according to claim 1,
   wherein the first information acquirer and the second information acquirer are different vehicle-mounted sensors;
   wherein the first information acquirer detects and obtains the information about the vehicle in real time; and
   wherein the second information acquirer acquires the vehicle condition information about the surrounding vehicles from the cloud in real time.

5. The method according to claim 1, wherein the vehicle condition information comprises at least one of:
   vehicle position information;

vehicle speed information;
acceleration information; and
steering information.

6. A driving behavior correction system based on the Internet of Vehicles, comprising:
- a first information acquirer for acquiring information about a vehicle in real time, wherein the information about the vehicle comprises: vehicle condition information about the vehicle, driver state information, and travelling road information about a road on which the vehicle travels, the driver state information comprising respiratory information, eye opening and closing information and attention information;
- a second information acquirer for acquiring vehicle condition information about the other surrounding vehicles on the travelling road in real time;
- a determination unit arranged in the vehicle or at a cloud for determining in real time, according to the information about the vehicle and the vehicle condition information about the surrounding vehicles, whether a driving behavior of the vehicle is dangerous;
- a prompt unit for issuing a driving behavior correction prompt to the driver of the vehicle if the driving behavior of the vehicle is dangerous, and not issuing the correction prompt if not; and
- a transmission unit configured to, if the determination unit determines in real time that the driving behavior of the vehicle is an illegal driving behavior according to the information about the vehicle and the vehicle condition information about the surrounding vehicles, upload the illegal driving behavior to the cloud, and send the illegal driving behavior to a vehicle management centre for recording so as to provide a basis for penalty on the driver, wherein the type of illegal driving behavior is pre-stored in the determination unit.

7. The system according to claim 6, wherein the transmission unit is further configured to download the correction prompt information from the cloud or read the correction prompt information from a memory in the vehicle, and to provide the correction prompt information to the prompt unit.

8. The system according to claim 6, wherein the first information acquirer and the second information acquirer are the same vehicle-mounted sensor.

9. The system according to claim 6, wherein
the first information acquirer and the second information acquirer are different vehicle-mounted sensors;
wherein the first information acquirer detects and obtains the information about the vehicle in real time; and
wherein the second information acquirer acquires the vehicle condition information about the surrounding vehicles from the cloud in real time.

10. The system according to claim 6, wherein vehicle condition information comprises at least one of:
vehicle position information;
vehicle speed information;
acceleration information; and
steering information.

* * * * *